(12) United States Patent
Takaso et al.

(10) Patent No.: US 7,884,245 B2
(45) Date of Patent: Feb. 8, 2011

(54) PROCESS FOR PRODUCING HYDRAZONE COMPOUND

(75) Inventors: Kiyokazu Takaso, Tsukuba (JP); Katsumi Abe, Koriyama (JP); Atsushi Takesue, Koriyama (JP)

(73) Assignee: Hodogaya Chemical Co., Ltd., Kawasaki-shi (JP)

( * ) Notice: Subject to any disclaimer, the term of this patent is extended or adjusted under 35 U.S.C. 154(b) by 268 days.

(21) Appl. No.: 11/571,399

(22) PCT Filed: Jun. 28, 2005

(86) PCT No.: PCT/JP2005/012275

§ 371 (c)(1), (2), (4) Date: Dec. 28, 2006

(87) PCT Pub. No.: WO2006/001537

PCT Pub. Date: Jan. 5, 2006

(65) Prior Publication Data

US 2008/0015387 A1 Jan. 17, 2008

(30) Foreign Application Priority Data

Jun. 29, 2004 (JP) .............................. 2004-191082

(51) Int. Cl.
*C07C 241/00* (2006.01)
*C07C 243/00* (2006.01)

(52) U.S. Cl. ..................................... 564/251

(58) Field of Classification Search ....................... None
See application file for complete search history.

(56) References Cited

U.S. PATENT DOCUMENTS 4,313,002 A * 1/1982 Symon et al. ................ 564/423
4,990,625 A * 2/1991 Arita et al. .................. 548/444

FOREIGN PATENT DOCUMENTS

| DE | 3029 742 A1 | 3/1982 |
|---|---|---|
| EP | 0 002 721 | 7/1979 |
| JP | 58-65261 | 4/1983 |
| JP | 1-224333 * | 7/1989 |
| JP | 1-224333 | 9/1989 |

OTHER PUBLICATIONS

Hall, N. Science, vol. 266, Oct. 7, 1994, pp. 32-34.*
Toshio, S. et al. Machine translation of JP 1-224333 (patent No. JP 2654057).*
English Abstract of JP5865261 published Apr. 16, 1983.

Database crossfire beilstein, XP-002476652, Database accession No. 668736, vol. 24, 1902 p. 1194.

* cited by examiner

*Primary Examiner*—Daniel M Sullivan
*Assistant Examiner*—Clinton Brooks
(74) *Attorney, Agent, or Firm*—Oblon, Spivak, McClelland, Maier & Neustadt, L.L.P.

(57) ABSTRACT

The present invention provides a process for producing a hydrazone compound represented by the general formula (5):

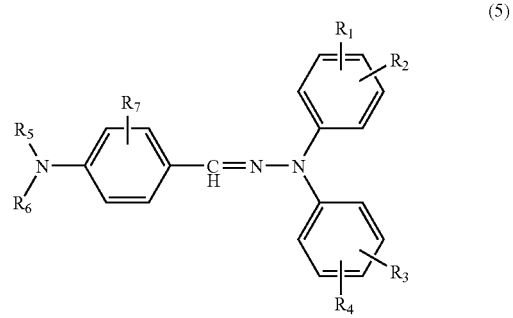

which comprises a step of condensing a hydrazine compound represented by the general formula (3):

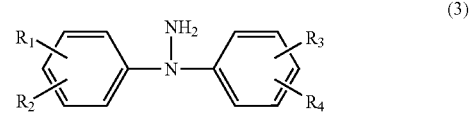

with a carbonyl compound represented by the general formula (4):

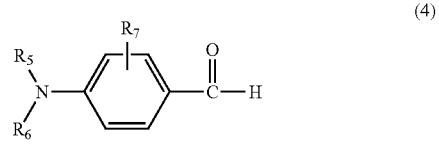

without taking the hydrazine compound out of a reactor. According to the invention, the target hydrazone compound can be obtained in high quality and in a high yield without taking the hydrazine compound out of the reactor at all, the hydrazine compound being a reaction intermediate which is structurally unstable and has a fear of influencing safety of workers owing to its toxicity (mutagenicity).

16 Claims, No Drawings

PROCESS FOR PRODUCING HYDRAZONE COMPOUND

TECHNICAL FIELD

The present invention relates to a process for producing a hydrazone compound useful as a photoconductive substance for use in an electrophotographic photoconductor.

BACKGROUND ART

Hitherto, hydrazone compounds are useful as photoconductive substances for use in electrophotographic photoconductors and their application to electrophotographic photoconductors and production processes have been disclosed (see, e.g., Patent Documents 1 to 5).

Patent Document 1: JP-A-06-166667
Patent Document 2: JP-A-02-308862
Patent Document 3: JP-A-02-308861
Patent Document 4: JP-A-61-23154
Patent Document 5: JP-A-60-255854

A hydrazone compound can be generally obtained by reducing an N-nitrosoamine compound to form a hydrazine compound and subsequently, after it is taken out as a hydrochloride salt, subjecting it to a condensation reaction with a carbonyl compound. In the case that it is intended to produce a hydrazone of industrially high quality in a high yield, it is required to obtain an easily oxidizable and unstable hydrazine compound in high quality and in a high yield at the completion of reaction. Furthermore, most of N-nitrosoamine compounds and hydrazine compounds are known to have toxicity (mutagenicity). Therefore, from the viewpoint of securing safety of workers, an exposure-preventing measure for workers against N-nitrosoamine compounds and hydrazine compounds is highly required.

As mentioned above, many of hydrazine compounds are very instable and easily oxidized and, in the case that hydrazine compounds are once taken out after N-nitrosoamine compounds are reduced, cases where it cannot be converted into hydrazone compounds or a remarkable decrease in yield may occur, so that this is mostly not suitable as an industrial production process for producing hydrazone compounds. There have been disclosed contrivances for avoiding these problems. For example, there has been proposed a process for producing a hydrazone compound, which comprises adding an sodium nitrite solution to a solution of 1 part by weight of N-phenyl-N-α or β-naphthylamine dissolved in 3 to 30 parts by weight of an organic acid to form an N-nitroso compound, subsequently reducing a solution containing the corresponding N-nitrosoamine, and condensing a reaction solution containing thus formed N-phenyl-N-α or β-naphthylhydrazine with a corresponding carbonyl compound (see, e.g., Patent Documents 6 and 7). In this process, since the N-nitrosoamine compound is reduced by a powder of a metal such as zinc and acetic acid, a filtration step of a residue of the reducing agent is indispensable in the post-treatment of the reaction. Due to the filtration step, oxidative decomposition of the hydrazone compound is still promoted and, as a result, a decrease in yield (about 60%) of the hydrazone compound as a final target compound and a decrease in quality thereof occur. Moreover, at the time of the filtering operation and the handling of the filtration residue, the exposure of workers to the hydrazone compound is unavoidable and thus, also from the viewpoint of securing safety of the workers, the process is not suitable as an industrial process for producing a hydrazone compound.

Hitherto, a hydrazine compound is obtained by reducing an N-nitrosoamine compound with zinc powder-acetic acid, sodium-ethanol, sodium-liquid ammonia, lithium aluminum hydride, or the like, separating the hydrazine compound from the reaction mixture, and further purifying it by salting-out, rectification distillation, chromatography, recrystallization, or the like. However, all these reducing agents are accompanied by danger in handling and also treatments of the residue of the reducing agents and the waste liquid after the reaction is vexatious and complex. Also, since the N—N bond is apt to be cleaved and the yield of the hydrazine compound is not sufficient, the process is industrially not satisfactory. A contrivance for avoiding the problems has been disclosed (see, e.g., Patent Document 8). The process disclosed in Patent Document 8 is a process for reducing an N-nitrosoamine compound with thiourea dioxide and an alkali in an aqueous medium. However, since the hydrazine compound is taken out, the exposure of workers to the hydrazine compound is unavoidable and also the cleavage of the N—N-bond can be not completely suppressed, so that the process is not suitable as an industrial process for producing a hydrazone compound.

Patent Document 6: JP-A-59-39860
Patent Document 7: JP-A-58-65261
Patent Document 8: JP-A-1-224333

DISCLOSURE OF THE INVENTION

An object of the invention is to provide a productions process capable of avoiding the exposure of workers to an N-nitrosoamine compound and a hydrazine compound as reaction intermediates to a hydrazone compound, generating no residue of a reducing agents and synthesizing a hydrazone compound of high quality in a high yield.

The prevention of the exposure of workers to an N-nitrosoamine compound and a hydrazine compound can be achieved by an operation that the compounds are not taken out of a reactor. Further, in order to produce a hydrazone compound of high quality in a high yield, after a hydrazine compound of high purity and high quality is obtained by selecting an appropriate reduction method of an N-nitrosoamine compound and optimizing reaction conditions, the aimed production can be achieved by converting the compound into the hydrazone compound as prompt as possible. The present inventors have found a one-pot synthetic process with one reactor capable of producing a hydrazone compound of high quality in a high yield without taking the reaction intermediates out of the reactor at all from the starting amine compound by adopting a reduction process with thiourea dioxide and an alkali as a reduction process of an N-nitrosoamine compound and further converting the resulting hydrazine compound, in the form of the solution as formed, into the hydrazone compound without taking the hydrazine compound out of the reactor. Thus, they have accomplished the invention.

Namely, the invention relates to a process for producing a hydrazone compound represented by the general formula (5):

(5)

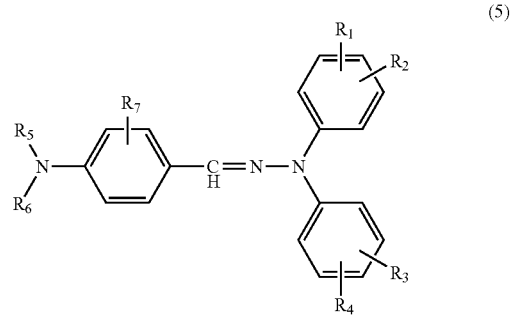

wherein $R_1$, $R_2$, $R_3$, $R_4$, $R_5$, $R_6$, and $R_7$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group, and $R_1$ and $R_2$ may be combined to form a ring and $R_3$ and $R_4$ may be combined to form a ring, which comprises:

a step of dissolving an amine compound represented by the general formula (1):

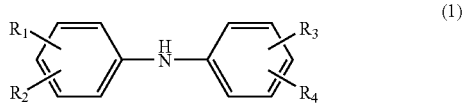
(1)

wherein $R_1$, $R_2$, $R_3$, and $R_4$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group, and $R_1$ and $R_2$ may be combined to form a ring and $R_3$ and $R_4$ may be combined to form a ring, in a mixed solvent of water and a water-miscible organic solvent arranged in a reactor and reacting the compound with an acid and sodium nitrite;

a step of adding thiourea dioxide and an alkali to a reaction solution containing an N-nitrosoamine compound formed by the reaction and represented by the general formula (2):

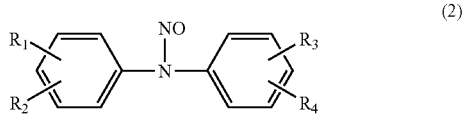
(2)

wherein $R_1$, $R_2$, $R_3$, and $R_4$ represent the same meanings as in the case of the general formula (1), to reduce the compound; and a step of condensing a hydrazine compound formed by the reduction and represented by the general formula (3):

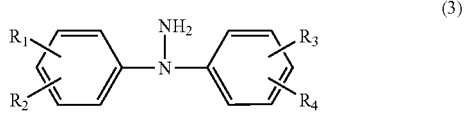
(3)

wherein $R_1$, $R_2$, $R_3$, and $R_4$ represent the same meanings as in the case of the general formula (1), with a carbonyl compound represented by the general formula (4):

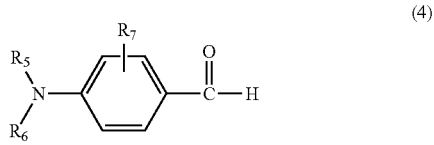
(4)

wherein $R_5$, $R_6$, and $R_7$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group, without taking the hydrazine compound out of the reactor (i.e., in the same reactor).

The invention provides a process for producing a hydrazone compound effective as a photoconductive material for use in a photographic photoconductor, which is capable of synthesizing the compound in high quality and in a high yield with little waste without taking a hydrazine compound as a reaction intermediate out of a reactor at all while safety of workers is highly secured. Thus, the industrial value of the process is high.

BEST MODE FOR CARRYING OUT THE INVENTION

In the hydrazone compound of the invention represented by the above general formula (5), the aralkyl group for $R_1$, $R_2$, $R_3$, $R_4$, $R_5$, $R_6$, and $R_7$ includes a benzyl group, a phenethyl group and the like, and the aryl group includes a phenyl group, a naphthyl group and the like. Moreover, the substituent for them includes a halogen atom (fluorine, chlorine, or bromine), a hydroxyl group, a vinyl group, a trifluoromethyl group, an alkyl group such as a methyl group, an ethyl group, an n-propyl group, a 2-propyl group, an n-butyl group, an isobutyl group, a secondary-butyl group or a tertiary-butyl group, an alkoxy group such as a methoxy group or an ethoxy group, or the above-mentioned aryl group.

The formation of an N-nitroso compound from the amine compound represented by the general formula (1) in the invention is carried out by adding an acid and sodium nitrite in a mixed solvent of water and a water-miscible organic solvent. Specific examples of the water-miscible organic solvent include alcohols such as methanol, ethanol, 2-propanol, and ethylene glycol, ethers such as dioxane, trioxane, ethylene glycol dimethyl ether, and tetrahydrofuran, and the like. Further, specific examples of the acid include inorganic acids such as hydrochloric acid and diluted sulfuric acid and organic acids such as formic acid and acetic acid. Sodium nitrite is added as an aqueous solution, and suitable is a concentration where no precipitation of sodium nitrite and the amine compound represented by the general formula (1) occurs. The thus formed N-nitrosoamine compound represented by the general formula (2) is subjected to a reduction reaction in the form of the reaction solution as formed without taking it out.

The reduction reaction of the N-nitrosoamine compound represented by the general formula (2) in the invention is carried out by adding an alkali and thiourea dioxide to the above reaction solution. The alkali usable is suitably sodium hydroxide but is not limited thereto and lithium hydroxide, potassium hydroxide, or the like can be also used. With regard to the amounts of thiourea dioxide and the alkali, it is suitable to use thiourea dioxide in an amount ranging from 2.0 to 2.5 mol relative to 1 mol of the amine compound represented by the general formula (1) and the alkali in an amount ranging from 4.5 to 6.0 mol in addition to the amount required for neutralization of the acid used for the formation of an N-nitroso compound. In the reduction with thiourea dioxide and the alkali according to the invention, the cleavage of the N—N bond also occurs as in the cases of the above-mentioned other reducing agents. However, this is not attributed to the action of the reducing agent itself but to the reaction of the formed hydrazine compound represented by the general formula (3) with the N-nitrosoamine compound represented by the general formula (2). Therefore, the regulation of the total amount of the mixed solvent for use in the nitroso compound-forming reaction is especially important from the viewpoint of suppressing the production of the amine compound represented by the general formula (1) as a by-product. It is suitable that the total amount of the mixed solvent is within the range of 14 to 31 times weight relative to the amount of thiourea dioxide, and the ratio of water is within the range of 30 to 60% by weight based on the mixed solvent. In particular, when the reduction reaction is carried out with an amount of the solvent lower than the regulation, the amine compound represented by the general formula (1) is remarkably produced as a by-product, so that the yield and quality of the hydrazone compound as a final product are deteriorated. Moreover, the production of the amine compound represented by the general formula (1) as a by-product is dependent on temperature and thus the reduction reaction is carried out suitably in the temperature range of 35 to 45° C., desirably in the temperature range of 38 to 43° C. When the reaction temperature is 45° C. or higher, remarkable production of the amine compound represented by the general formula (1) as a by-product occurs. On the other hand, a remarkable decrease in reaction rate is observed at a temperature of 35° C. or lower.

The solution of the hydrazine compound represented by the general formula (3) is obtained by removing the water-miscible organic solvent by distillation after the completion of the reduction reaction and extracting the residue with a suitable organic solvent. The organic solvent for extraction is suitably an organic solvent having a specific gravity of less than 1.0, which dissolves the hydrazine compound represented by the general formula (3) and the carbonyl compound represented by the general formula (4) and which is not miscible with water. Specific examples include ethers such as diethyl ether and isopropyl ether, aromatic hydrocarbons such as toluene and xylene, and the like.

The hydrazone compound as the final target compound in the invention is obtained by reacting the extraction solution of the hydrazine compound represented by the general formula (3) with the carbonyl compound represented by the general formula (4). The dehydrative condensation reaction can be accelerated by adding an acid as commonly known and, for example, an inorganic acid such as hydrochloric acid or sulfuric acid or an organic acid such as acetic acid is used. The reaction well proceeds at room temperature without heating but heating may be conducted in order to accelerate the reaction. In either case, the reaction time is from 1 to 5 hours. After the completion of the reaction, the final target compound can be taken out by filtering off the precipitated crystals or, in the case where crystals are not precipitated or the precipitation of crystals is insufficient, by filtering off the crystals formed through addition of an alcohol such as methanol or ethanol, a hydrous alcohol or the like, or by partially removing the organic solvent by distillation under reduced pressure and then dispersing the residue into an alcohol such as methanol or ethanol, a hydrous alcohol or the like and filtering the resulting crystals.

The hydrazone compounds to be produced by the production process of the invention include the following: p-diethylaminobenzaldehyde=dipenylhydrazone, p-diphenylaminobenzaldehyde=dipenylhydrazone, p-(p-tolyl)phenylaminobenzaldehyde-dipenylhydrazone, p-di(p-tolyl)aminobenzaldehyde=dipenylhydrazone, p-(p-methoxyphenyl)phenylaminobenzaldehyde=dipenylhydrazone, 2-methyl-4-dibenzylaminobenzaldehyde=dipenylhydrazone, p-diphenylaminobenzaldehyde=di-(p-tolyl)hydrazone, p-diphenylaminobenzaldehyde=bis(6-tetralyl)hydrazone, p-diphenylaminobenzaldehyde=bis(5-indanyl)hydrazone, p-dibenzylaminobenzaldehyde=bis(6-tetralyl)hydrazone, p-dimethylaminobenzaldehyde=bis(2,4-dimethylphenyl)hydrazone, p-bis(2-methyl-4-methoxyphenyl) aminobenzaldehyde=diphenylhydrazone, p-bis(2,4-dimethylphenyl)aminobenzaldehyde=di(p-tolyl)hydrazone.

EXAMPLE

The following will explain the present invention in detail with reference to Examples but the invention is not limited to Examples.

Example 1

Into a 500 ml four-neck flask were added 16.9 g (100 mmol) of diphenylamine, 15.1 g (251 mmol) of acetic acid, and 207 g of methanol and the whole was dissolved under stirring. Thereto was added 13.8 g (200 mmol) of sodium nitrite dissolved in 57 g of water, followed by stirring at 15 to 20° C. for 3 hours. After the disappearance of diphenylamine was confirmed by high-performance liquid chromatography, 26.1 g (653 mmol) of sodium hydroxide dissolved in 119 g of water and 259 g (240 mmol) of thiourea dioxide were added, followed by stirring at 38 to 43° C. for 3 hours. After the disappearance of N-nitrosodiphenylamine was confirmed by high-performance liquid chromatography, methanol was removed by distillation under reduced pressure, followed by extraction with 120 g of toluene to obtain a toluene solution of 1,1-diphenylhydrazine. The compositional ratio excluding toluene determined by high-performance liquid chromatography was 88.9% of 1,1-diphenylhydrazine and 10.2% of diphenylamine.

Example 2

To the toluene solution of 1,1-diphenylhydrazine obtained in Example 1 were added 24.3 g (89 mmol) of p-diphenylaminobenzaldehyde and 3.0 g (50 mmol) of acetic acid, followed by stirring at 40 to 45° C. for 2 hours. After the disappearance of 1,1-diphenylhydrazine was confirmed by high-performance liquid chromatography, 110 g of methanol was added and precipitated crystals were filtered off to obtain 36.5 g of p-diphenylaminobenzaldehyde=diphenylhydrazone. The yield was 83.1% based on the starting diphenylamine and the purity determined by high-performance liquid chromatography was 99.4%.

Example 3

To the toluene solution of 1,1-diphenylhydrazine obtained in Example 1 were added 26.8 g (89 mmol) of p-di(p-tolyl)aminobenzaldehyde and 3.0 g (50 mmol) of acetic acid, followed by stirring at 40 to 45° C. for 1 hours. After the disappearance of 1,1-diphenylhydrazine was confirmed by high-performance liquid chromatography, 100 g of methanol was added and precipitated crystals were filtered off to obtain 38.6 g of p-di(p-tolyl)aminobenzaldehyde=diphenylhydrazone. The yield was 82.7% based on the starting diphenylamine and the purity determined by high-performance liquid chromatography was 99.7%.

Example 4

To the toluene solution of 1,1-diphenylhydrazine obtained in Example 1 were added 28.0 g (89 mmol) of 2-methyl-4-dibenzylaminobenzaldehyde and 3.0 g (50 mmol) of acetic acid, followed by stirring at 40 to 45° C. for 3 hours. After the disappearance of 1,1-diphenylhydrazine was confirmed by high-performance liquid chromatography, toluene was partially removed by distillation under reduced pressure and 100 g of methanol was added and dispersed and resulting crystals were filtered off to obtain 39.2 g of 2-methyl-4-dibenzylaminobenzaldehyde=diphenylhydrazone. The yield was 81.5% based on the starting diphenylamine and the purity determined by high-performance liquid chromatography was 99.3%.

Example 5

To the toluene solution of 1,1-diphenylhydrazine obtained in Example 1 were added 15.7 g (89 mmol) of p-diethylaminobenzaldehyde and 3.0 g (50 mmol) of acetic acid, followed by stirring at 40 to 45° C. for 3 hours. After the disappearance of 1,1-diphenylhydrazine was confirmed by high-performance liquid chromatography, toluene was partially removed by distillation under reduced pressure and 105 g of methanol was added and dispersed and resulting crystals were filtered off to obtain 29.0 g of p-diethylaminobenzaldehyde=diphenylhydrazone. The yield was 83.8% based on the starting diphenylamine and the purity determined by high-performance liquid chromatography was 99.3%.

Comparative Example 1

Into a 300 ml four-neck flask were added 16.9 g (0.1 mol) of diphenylamine and 118 g (2.0 mol) of acetic acid, and the whole was dissolved under stirring. Thereto was added 15.2 g (0.2 mol) of sodium nitrite dissolved in 22 g of waters followed by stirring at 30 to 35° C. for 6 hours. Then, 19.6 g (0.3 mol) of zinc powder was added to the reaction solution containing N-nitrosodiphenylamine in the range of 20 to 25° C. to effect reduction. The reaction was traced by thin-layer chromatography. After the completion of the reduction, the reduced residue was immediately filtered. Then, 24.3 g (0.09 mol) of p-diphenylaminobenzaldehyde was added to the filtrate, followed by stirring at 15 to 20° C. for 1 hour. After the disappearance of N-nitrosodiphenylamine was confirmed by thin-layer chromatography, the reaction solution was poured into water, followed by extraction with 120 g of toluene. Then, 110 g of methanol was added and precipitated crystals were filtered off to obtain 25.8 g of p-diphenylaminobenzaldehyde=diphenylhydrazone. The yield was 58.8% based on the starting diphenylamine and the purity determined by high-performance liquid chromatography was 98.4%.

Comparative Example 2

Into a 1000 ml four-neck flask were added 16.9 g (100 mmol) of diphenylamine, 15.1 g (251 mmol) of acetic acid, and 256 g of methanol, and the whole was dissolved under stirring. Thereto was added 13.8 g (200 mol) of sodium nitrite dissolved in 57 g of water, followed by stirring at 15 to 20° C. for 8 hours. After the disappearance of diphenylamine was confirmed by high-performance liquid chromatography, 26.1 g (653 mmol) of sodium hydroxide dissolved in 225 g of water and 25.9 g (240 mmol) of thiourea dioxide were added, followed by stirring at 38 to 43° C. for 3 hours. After the disappearance of N-nitrosodiphenylamine was confirmed by high-performance liquid chromatography, methanol was removed by distillation under reduced pressure, followed by extraction with 100 g of diethyl ether. The compositional ratio determined by high-performance liquid chromatography was 88.9% of 1,1-diphenylhydrazine and 11.0% of diphenylamine. After the extraction solution was subjected to water removal over anhydrous magnesium sulfate, hydrogen chloride gas was introduced into the solution and precipitated crystals were filtered off to obtain 17.8 g of 1,1-diphenylhydrazine hydrochloride. The yield was 80.8% based on the starting diphenylamine.

To a 300 ml four-neck flask were added 17.0 g (77 mmol) of 1,1-diphenylhydrazine hydrochloride obtained in Comparative Example 2, 21.1 g (77 mmol) of p-diphenylaminobenzaldehyde, and 70 g of DMF, followed by stirring at 40 to 45° C. for 3 hours. The reaction was traced by thin-layer chromatography. After, the completion of the reaction, 100 g of methanol was added and precipitated crystals were filtered off to obtain 32.3 g of p-diphenylaminobenzaldehyde=diphenylhydrazone. The yield was 95.4% based on the starting 1,1-diphenylhydrazine, the over all yield from the starting diphenylamine was 77.0%, and the purity determined by high-performance liquid chromatography was 98.2%.

INDUSTRIAL APPLICABILITY

The process for producing a hydrazone compound in the present invention is useful since the target hydrazone compound can be obtained in high quality and in a high yield without taking the hydrazine compound out of the reactor at all, the hydrazine compound being a reaction intermediate which is structurally unstable and has a fear of influencing safety of workers owing to its toxicity (mutagenicity).

While the invention has been described in detail and with reference to specific examples thereof, it will be apparent to one skilled in the art that various changes and modifications can be made therein without departing from the spirit and scope thereof.

The present application is based on Japanese Patent Application No. 2004-191082 filed on Jun. 29, 2004, and the contents are incorporated herein by reference.

The invention claimed is:

1. A process for producing a hydrazone compound represented by the general formula (5):

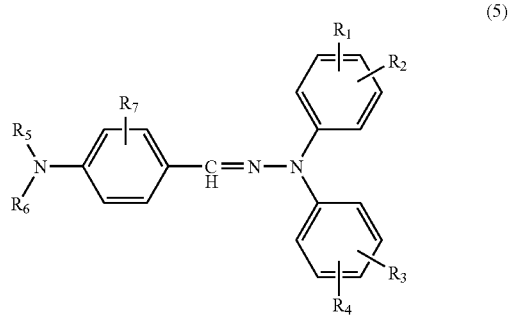

wherein $R_1$, $R_2$, $R_3$, $R_4$, $R_5$, $R_6$, and $R_7$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group, and $R_1$ and $R_2$ may be combined to form a ring and $R_3$ and $R_4$ may be combined to form a ring, said process comprising:

a) dissolving an amine compound represented by the general formula (1) in a mixed solvent of water and a water-miscible organic solvent arranged in a reactor, and reacting the compound with an acid and sodium nitrite, to obtain a reaction solution containing an N-nitrosoamine compound, wherein said amine compound represented by the general formula (1) is as follows:

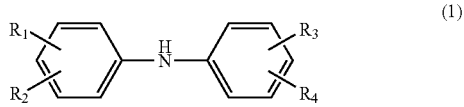

(1)

wherein $R_1$, $R_2$, $R_3$, and $R_4$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group, and $R_1$ and $R_2$ may be combined to form a ring and $R_3$ and $R_4$ may be combined to form a ring;

said N-nitrosoamine compound being represented by the general formula (2):

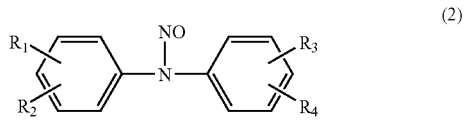

(2)

wherein $R_1$, $R_2$, $R_3$, and $R_4$ represent the same meanings as in the case of the general formula (1);

b) adding thiourea dioxide and an alkali to said reaction solution containing said N-nitrosoamine compound of formula (2) to reduce said N-nitrosoamine compound in said reactor, and to obtain a hydrazine compound of formula (3);

wherein the hydrazine compound of formula (3) is as follows

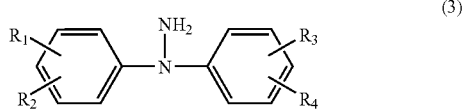

(3)

wherein $R_1$, $R_2$, $R_3$, and $R_4$ represent the same meanings as in the case of the general formula (1); and c) condensing said hydrazine compound of formula (3) with a carbonyl compound represented by the general formula (4), without taking the hydrazine compound out of said reactor, to obtain said hydrazone compound of formula (5);

wherein the carbonyl compound represented by the general formula (4) is as follows

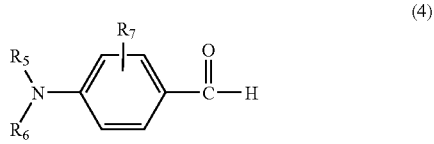

(4)

wherein $R_5$, $R_6$, and $R_7$ may be the same or different and each represents a hydrogen atom, a methyl group, an ethyl group, an n-propyl group, a 2-propyl group, an n-butyl group, an isobutyl group, a secondary-butyl group, a tertiary-butyl group, a methoxy group, an ethoxy group, a substituted or unsubstituted aralkyl group, or a substituted or unsubstituted aryl group; and wherein the condensing c) is conducted by
removing the water-miscible organic solvent by distillation from the mixed solvent of a reaction mixture obtained in step b) to obtain a distillation residue, said distillation residue comprising said hydrazine compound, adding an organic solvent to said distillation residue for extraction of the hydrazine compound from said distillation residue, and then reacting said hydrazine compound in a solution obtained by the extraction with the carbonyl compound represented by the general formula (4).

2. The process for producing a hydrazone compound according to claim 1, wherein the total amount of the mixed solvent is within the range of 14 to 31 times weight relative to the amount of thiourea dioxide used in the reduction reaction of the N-nitrosoamine compound represented by the general formula (2) and the ratio of water is within the range of 30 to 60% by weight relative to the mixed solvent.

3. The process for producing a hydrazone compound according to claim 1, wherein the reduction reaction of the N-nitrosoamine compound represented by the general formula (2) is carried out at the reaction temperature range of 35 to 45° C.

4. The process for producing a hydrazone compound according to claim 1, wherein the reduction reaction of the N-nitrosoamine compound represented by the general formula (2) is carried out at the reaction temperature range of 38 to 43° C.

5. The process for producing a hydrazone compound according to claim 1, wherein in the hydrazone compound of formula (5), the aralkyl group for $R_1$, $R_2$, $R_3$, $R_4$, $R_5$, $R_6$, and $R_7$ is a benzyl group or a phenethyl group, and the aryl group is a phenyl group or a naphthyl group.

6. The process for producing a hydrazone compound according to claim 1, wherein in the hydrazone compound of formula (5), a substituent for $R_1$, $R_2$, $R_3$, $R_4$, $R_5$, $R_6$, and $R_7$ is a halogen atom, a hydroxyl group, a vinyl group, a trifluoromethyl group, an alkyl group, an alkoxy group or an aryl group.

7. The process for producing a hydrazone compound according to claim 1, wherein the water-miscible organic solvent is an alcohol, or ether.

8. The process for producing a hydrazone compound according to claim 1, wherein an amounts of thiourea dioxide is from 2.0 to 2.5 mol relative to 1 mol of the amine compound represented by the general formula (1).

9. The process for producing a hydrazone compound according to claim 1, wherein an amount of alkali is from 4.5 to 6.0 mol in addition to the amount required for neutralization of the acid used for the formation of an N-nitroso compound.

10. The process for producing a hydrazone compound according to claim 1, wherein the organic solvent for extraction has a specific gravity of less than 1.0, dissolves the hydrazine compound represented by the general formula (3) and the carbonyl compound represented by the general formula (4) and is not miscible with water.

11. The process for producing a hydrazone compound according to claim 1, wherein the organic solvent for extraction is an ether or an aromatic hydrocarbon.

12. The process for producing a hydrazone compound according to claim 1, wherein condensation reaction proceeds at room temperature without heating.

13. The process for producing a hydrazone compound according to claim 1, wherein hydrazone compound is p-diethylaminobenzaldehyde=diphenylhydrazone, p-diphenylaminobenzaldehyde=diphenylhydrazone, p-(p-tolyl)phenylaminobenzaldehyde-diphenylhydrazone, p-di(p-tolyl)aminobenzaldehyde=diphenylhydrazone, p-(p-methoxyphenyl)phenylaminobenzaldehyde=diphenylhydrazone, 2-methyl-4-dibenzylaminobenzaldehyde=diphenylhydrazone, p-diphenylaminobenzaldehyde=di-(p-tolyl)hydrazone, p-diphenylaminobenzaldehyde=bis(6-tetralyl)hydrazone, p-diphenylaminobenzaldehyde=bis(5-indanyl)hydrazone, p-dibenzylaminobenzaldehyde=bis(6-tetralyl)hydrazone, p-dimethylaminobenzaldehyde=bis(2,4-dimethylphenyl)hydrazone, p-bis(2-methyl-4-methoxyphenyl)aminobenzaldehyde=diphenylhydrazone or p-bis(2,4-dimethylphenyl)aminobenzaldehyde=di(p-tolyl)hydrazone.

14. The process for producing a hydrazone compound according to claim 1, wherein said water-miscible organic solvent is methanol.

15. The process for producing a hydrazone compound according to claim 1, wherein said organic solvent for extracting the hydrazine compound is toluene.

16. The process for producing a hydrazone compound according to claim 1, the solvent added for extraction of said hydrazine compound is different from the solvent distilled off from the mixed solvent of said reaction mixture obtained in step b).

* * * * *